United States Patent [19]

Sbarra

[11] Patent Number: 5,010,016
[45] Date of Patent: Apr. 23, 1991

[54] METHOD AND TEST KIT FOR THE DETERMINATION OF FETAL PULMONARY MATURITY STATUS

[76] Inventor: Anthony J. Sbarra, 54 Cypress Rd., Milton, Mass. 02186

[21] Appl. No.: 391,411

[22] Filed: Aug. 9, 1989

[51] Int. Cl.$^5$ .................. B01L 3/14; G01N 21/76; G01N 33/48; G01N 33/92
[52] U.S. Cl. ................................ 436/63; 73/61 R; 73/864.91; 435/4; 436/71; 436/172; 436/907
[58] Field of Search .................. 436/63, 71, 183, 907, 436/172; 435/4; 422/61; 73/61 R, 864.91, 426

[56] References Cited

U.S. PATENT DOCUMENTS

| | | | |
|---|---|---|---|
| 4,233,032 | 11/1980 | Statland et al. | 436/63 |
| 4,257,771 | 3/1981 | Yee | 436/71 |
| 4,388,412 | 6/1983 | Yabusaki | 436/71 |
| 4,391,780 | 7/1983 | Boris | 422/102 |
| 4,459,362 | 7/1984 | Yabusaki | 436/71 |
| 4,547,464 | 10/1985 | Socol | 436/71 |
| 4,784,945 | 11/1988 | Artiss et al. | 436/907 |
| 4,784,961 | 11/1988 | Russell | 436/63 |
| 4,820,628 | 4/1989 | Weitz | 436/71 |
| 4,839,294 | 6/1989 | Almog et al. | 436/71 |

FOREIGN PATENT DOCUMENTS

1057015  11/1983  U.S.S.R. .................. 436/907

OTHER PUBLICATIONS

Sbarra, Anthony J. et al., Correlation Between Amniotic Fluid Optical Density and L/S Ratio, "Obstetrics and Gynecology", vol. 48, No. 5, pp. 613-615, 11/76.
Sbarra, Anthony J. et al., Relation Between Optical Density at 650 nm and L/S Ratios, "Obstetrics-Gynecology", vol. 50, No. 6, pp. 723-724, 12/77.
Sbarra, Anthony J. et al., Positive Correlation of Optical Density at 650 nm. with Lecithin/Sphingomyelin Ratios in Amniotic Fluid, "American Journal of Obstetrics and Gynecology", vol. 130, No. 7, pp. 788-790, 4/1/78.
Sbarra, A. J. et al., The Effect of Cervical/Vaginal Secretions on Measurements of Lecithin/Sphingomyelin Ratio and Optical Density at 650 NM, "American Journal of Obstetrics and Gynecology", vol. 139, No. 2, pp. 214-216, 1/15/81.
Sbarra, Anthony J. et al., Surfactans, L/S Ratio, Amniotic Fluid Optical Density and Fetal Pulmonary Maturity, "The Journal of Reproductive Medicine for the Obstetrician and Gynecologist", vol. 27, No. 1, pp. 34-38, 1/82.
Sbarra, Anthony J. et al., Amniotic Fluid Optical Density and Fetal Pulmonary Status, "Letters", vol. 61, No. 5, pp. 669-670, 5/83.
Sbarra, Anthony J. et al., Correlation of Amniotic Fluid Optical Density at 650 nm and Lecithin/Sphingomyelin Ratios with Phosphatidylglycerol, "American Journal of Obstetrics and Gynecology", vol. 149, No. 7, pp. 740-743, 8/1/84.
Cetrulo, Curtis L. et al, Positive Correlation Between Mature Amniotic Fluid Optical Density Readings and the Absence of Neonatal Hyaline Membrane Disease, "The Journal of Reproductive Medicine", vol. 30, No. 12, pp. 929-932, 12/85.
Chaudhury, A. K. et al, Determination of Fetal Pulmonary Maturity Status by Visual Observation of Amniotic Fluid, Society of Perinatal Obstetricians, Ninth Annual Meeting, New Orleans, Louisiana, Feb. 1-4, 1989, p. 346.

Primary Examiner—Robert J. Hill, Jr.
Assistant Examiner—Kimberly A. Trautman
Attorney, Agent, or Firm—Richard P. Crowley

[57] ABSTRACT

A test kit and method of determining fetal pulmonary maturity which method comprises visually comparing a test amniotic fluid with selected positive and negative control samples and which test kit includes selected positive and negative control samples for comparison purposes.

12 Claims, 1 Drawing Sheet

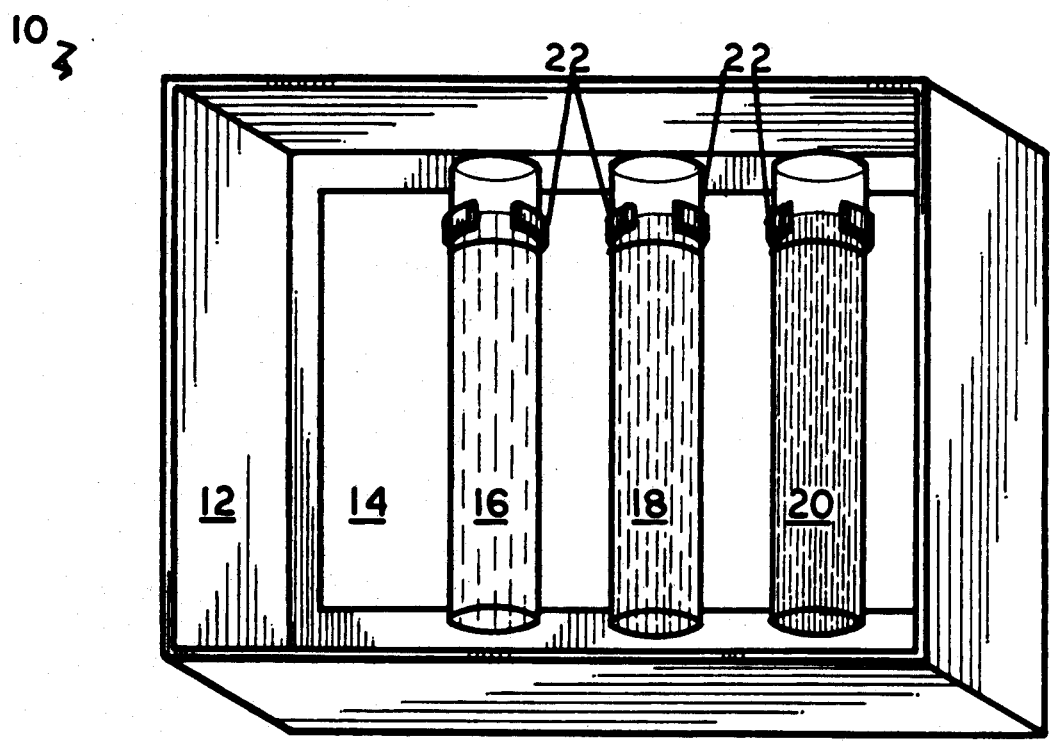

METHOD AND TEST KIT FOR THE DETERMINATION OF FETAL PULMONARY MATURITY STATUS

BACKGROUND OF THE INVENTION

Lecithin/Sphingomylin ratios (L/S) and Phosphatidyl glycerol (PG) determinations are generally the most widely used and accepted labortory tests for the determination of fetal pulmonary maturity status. Their relatively complex methodology, however, limits their availability. Ideally, the tests should be available on damand. Since this is essentially an impossibility, except in a few large academic centers, an alternate test methodology has been sought by a number of different investigators. An accurate, simple, economical and rapid method that can be used on damand basis has been developed. This method involves centrifugation of pigment-free amniotic fluid for exactly ten minutes at $2000 \times g$. The spun optical density (OD) at 650 nm is then determined on the supernatent. If the spun OD 650 is greater than or equal to 0.15, fetal pulmonary maturity is assured, while if the spun OD 650 is less than 0.15, fetal pulmonary immaturity is likely.

While the further centrifugation test method is of value, the test still requires laboratory equipment and test procedures which are not always workable or available on demand and requires a finite amount of time to carry out the test.

It is desired to provide a very rapid, economical and effective test method and kit which does not require laboratory test equipment or laboratory procedures.

SUMMARY OF THE INVENTION

The invention relates to a method and test kit for the determination of fetal pulmonary maturity status by visual observation of amniotic fluid.

The test method comprises determining the fetal pulmonary maturity status of an amniotic test fluid sample with a high degree of accuracy generally greater than about seventy-five percent by visual observation of the test sample in comparison to positive and negative control samples. The test method includes comparing a pigment-free amniotic fluid test sample from a patient to a positive control sample which positive control sample mimics an optical density (OD) of a selected value, e.g. of about 0.80 at 650 nm, which positive control sample indicates fetal pulmonary maturity and to a negative control sample which negative control sample mimics an optical density (OD) of a lower selected value, e.g. of about 0.50 at 650 nm, which indicates fetal pulmonary immaturity. It has been found that the selected optical density values provide for a reliable indication of fetal maturity or immaturity. When an amniotic fluid test sample does not fall within the selected OD values, then a laboratory test, such as centrifugation, may be employed to evaluate fetal maturity.

The test ket of the invention comprises the positive and negative control samples of defined and selected optical density so that the control samples, generally in transparent plastic or glass tube form, may be visually compared to the test fluid in the same form. Optionally, the test kit may contain a plurality of positive and/or negative control samples of selected optical density if a more detailed and accurate determination is required. In addition, the test kit may comprise a container for the control samples, for example, mounted in the container or other display means optionally with means to place the test fluid in a container which is adjacent to or between the control samples for ease in visual comparison. Also, the test kit may contain a selected background, such as a black, white or other sheet, for ease in comparing the test sample with the control samples.

The control samples may be in solid, gel, liquid, emulsion, suspension or other form while the amniotic fluid test sample is in liquid form. The control sample may be prepared using a variety of materials provided the optical density of the control sample so achieved mimics the selected essential OD's of $\geq 0.08$ (+) and $<0.50$ (−), or other selected OD control values.

In one embodiment, the control samples may be prepared by the use of selected concentrations of synthetic or natural polymers or gums, such as by the use of purified agar in water, to form a solid-gel type control sample in a transparent vial. In another embodiment, it has been found that a mixture of sulfuric acid and barium chloride may be reacted together to form an insoluble liquid mixture containing barium sulfate in a control sample vial. The control samples so prepared are liquid suspensions of the desired OD depending upon the amount of reagents employed, but such control sample must be shaken prior to comparison with the amniotic test fluid. The solid agar-type, sealed control samples have been found to be safe, stable and effective controls.

The invention will be described for the purposes of illustration only in connection with certain embodiments; however, it is recognized that those persons skilled in the art may make various changes, additions, modifications and improvements to the embodiments, all falling within the spirit and scope of the invention.

BRIEF DESCRIPTION OF THE DRAWING

The drawing is a schematic illustration of the test kit of the invention.

DESCRIPTION OF THE EMBODIMENTS

The drawing shows a test kit 10 which comprises a box-like container 12 with a white background view paper sheet 14 and with three parallel transparent, sealed plastic vials 16, 18 and 20 retained in position by U-shaped tension retainers 22 secured to the surface of the container 12. Vial 16 comprises a solid agar negative control sample of OD 0.50 at 650 nm of 0.75% by weight of purified agar, and vial 20 comprises a solid agar positive control sample of OD 0.80 at 650 nm of 3.0% by weight of purified agar. Vial 18 is the illustrated amniotic test fluid to be visually compared in optical density with vials 16 and 20 to determine fetal maturity.

One hundred and sixty-seven amniotic fluid samples were obtained by transabdominal amniocentesis. The fluids were obtained from patients within the following disorders: toxemia, intrauterine growth retardation, chronic hypertension, premature labor and scheduled repeat Cesarean section. Optical density measurements of all fluids were made within 1 to 2 hours in a 1 cm light-path cuvette against distilled water at 650 nm in a Beckman DB spectrophotometer. Spun OD 650 measurements were made on these fluids after upspun OD 650 readings were taken. Centrifugation was carried out in International Model PR-J refrigerated centrifuge at 3200 rpm ($2000 \times g$) for ten minutes. Specimens containing gross meconium, grossly hemolyzed blood or frozen and thawed fluid were excluded from this test.

Positive and negative controls of fetal pulmonary maturity were made by dissolving different concentrations of purified agar in distilled water.

A positive control sample of 3.0% by weight of Difco purified agar and a negative control sample of 0.75% by weight of Difco purified agar were prepared as follows:
- 3 gms agar dissolved in 100 ml distilled water for positive control; and
- 0.75 gms agar dissolved in 100 ml distilled water for negative control.

The different concentrations of agar, i.e. 3 gms, 0.75 gms, are placed in 250 ml flask and placed in a boiling water bath until agar is dissolved. Approximately 8–10 ml of each is placed in red top, sterile vacutained tubes. Rubber stoppers are loosely placed in tubes and all tubes are autoclaved for 15 minutes at 121° C. After cooling, tops are secured in place and tape is placed around them to delay drying. Frequently, amniotic fluid will have a very faint, yellow-type color or it may be tinged with blood (pink). In those cases, it is possible that soluble coloring agents of these colors can be added to the agar tubes before solidification. This will neutralize or mimic the colors in the amniotic fluid and allow comparison of the turbidity of the colored amniotic fluid with the similarly colored positive and negative controls.

Ninety-four amniotic test fluids were visually compared to the positive and negative control tubes and recorded as mature or immature. L/S ratios and PG analysis were subsequently performed.

A total of 167 fluids were analyzed for OD 650, L/S ratio, PG and upspun OD 650. Eighty-seven of these fluids has an unspun OD 650≧0.80, an L/S ≦2.0, a spun OD 650≧0.15 and PG present. Thirty-two of the fluids had an unspun OD 650<0.05, an L/S ratio <2.0, a spun OD 650<0.15 and PG absent. These data are set forth in Table 1.

The Table 2, it may be seen that 26 fluids had an unspun OD 650>0.50 and <0.80. These fluids had a spun OD 650≧0.15, L/S ratio ≧2.0 and PG present. On the other hand, 22 fluids with the same upspun OD 650 values had spun OD 650<0.15, L/S ratio <2.0 and PG absent.

From these results, a positive and a negative control sample were made. A tube having an OD 650 equivalent to 0.80 was called a positive control. A tube having an OD 650 equivalent to 0.50 was made and called a negative control. Ninety-four amniotic fluid samples were judged to be mature or immature by visual observation before laboratory testing was initiated, and the test results are noted in Table 3. Visually, 65 fluids were judged to be mature. Subsequent laboratory testing reveals that six of the fluids did not have mature indices. This resulted in a nine percent false positive rate. Twenty-nine fluids were visually judged to be immature. Laboratory testing however indicated pulmonary maturity in six of these fluids, resulting in a twenty-one percent false negative rate.

TABLE 1

| Amniotic Fluids with Unspun OD 650 > 0.80 and < 0.50 | | | | |
|---|---|---|---|---|
| # of pts. | Unspun OD 650 | Spun OD 650 | L/S | PG |
| 87 | ≧0.80 | ≧0.15 | ≧2.0 | present |
| 32 | <0.50 | <0.15 | <2.0 | absent |

TABLE 2

| Amniotic Fluids with Unspun OD 650 > 0.50 and < 0.80 | | | | |
|---|---|---|---|---|
| # of pts. | Unspun OD 650 | Spun OD 650 | L/S | PG |
| 26 | >0.50 < 0.80 | ≧0.15 | ≧2.0 | present |
| 22 | >0.50 < 0.80 | <0.15 | <2.0 | absent |

TABLE 3

Comparison between Visual Observation of Amniotic Fluid and OD 650, L/S and PG Analysis

| | Visual Observation | | | |
|---|---|---|---|---|
| Laboratory Anaylsis[1] | Mature | Immature | False Positive | False Negative |
| OD 650, PG L/S; mature | 59 | 6 | 9% | — |
| OD 60, PG L/S; immature | 6 | 23 | — | 21% |

[1] Mature OD 650 > 0.15, L/S > 2.0, PG present
Immature OD 650 < 0.15, L/S < 2.0, PG absent
All three determinations not reported in all cases OD 650 determinations require that amniotic fluid must be centrifuged for a ten minute period at precisely 2000×g. It has been discovered now that surprisingly by simply looking at the unspun amniotic fluid, one could frequently predict fetal pulmonary maturity status. A cloudy fluid would invariably be associated with a spun OD 650 of ≧0.15, an L/S ratio of ≧2.0 and the presence of PG. The OD 650 of uncentrifuged (unspun) amniotic fluid has been measured. Out of 167 fluids, fifty-two percent had an unspun OD 650 of ≧0.80. All of the fluids subsequently were noted to have mature indices. Nineteen percent of the fluids had an unspun OD 650<0.50. These fluids had immature indices. Twenty-eight percent of the fluids had unspun OD 650>0.50 and <0.80. Fifty-four percent of these fluids showed mature indices and forth-six percent had immature indices. Interestingly, in these cases, the only laboratory test needed was the spun OD 650 (Table 3). From these data, positive and negative control standards have been established. The positive control was set to mimic visually a pigment-free, unspun amniotic fluid OD 650 of 0.80. The negative control was set to mimic at an OD 650 of 0.50. Amniotic fluids that compared with the positive control were considered to have mature fetal pulmonary indices. Fluids having turbidity compared to the negative control were considered to have immature pulmonary indices. The positive and negative controls permit the rapid and easy visual comparison of the test amniotic fluid with the controls for a determination of maturity status. The test kit and method permit the rapid determination of whether an amniotic fluid will have mature indices by simply observing the degree of turbidity and comparing with a positive and a negative control. The method and test kit are particularly valuable in areas where laboratory testing is difficult to obtain.

What is claimed is:

1. A method for the determination of fetal pulmonary maturity from an amniotic fluid test sample, which method comprises:
   visually comparing a pigment-free amniotic fluid test sample from a patient to a positive control sample which mimics an optical density (OD) of about 0.80 at 650 nm which indicates fetal pulmonary maturity and a negative control sample which mimics an optical density (OD) of about 0.50 at 650 nm which indicates fetal pulmonary immaturity and from said comparing providing an indication of the fetal pulmonary status of the fetus.

2. The method of claim 1 which includes centrifugally testing those test samples which are visually observed to have an optical density (OD) between the positive and negative control samples to determine fetal pulmonary maturity.

3. The method of claim 1 wherein the control samples comprise a solid agar sample in a transparent vial.

4. The method of claim 1 wherein the control sample comprises an aqueous suspension of barium sulfate prepared by the reaction of a barium salt and sulfuric acid in a transparent vial and which includes shaking the control sample suspension prior to comparing the amniotic fluid test sample with the control samples.

5. The method of claim 1 which includes comparing the control samples which are in transparent vials to the test sample which is in a transparent vial where the test sample is adjacent to or between control sample vials and all the vials are compared against a selected background.

6. The method of claim 1 wherein the positive control sample comprises about 3.0% by weight of purified agar in water and the negative control sample comprises about 0.75% by weight of purified agar in water.

7. The method of claim 6 which includes adding a coloring agent to the purified agar control sample to mimic the color of the amniotic fluid to be tested.

8. A test kit for the determination of fetal pulmonary maturity from an amniotic fluid test sample, which test kit comprises in combination:
(a) a positive control sample constructed so as to mimic an optical density (OD) of about 0.80 at 650 nm which indicates fetal pulmonary maturity; and
(b) a negative control sample constructed so as to mimic an optical density (OD) of about 0.50 at 650 nm which indicates fetal pulmonary immaturity
whereby visually comparing the test sample with the positive and negative control samples provides an indication of fetal pulmonary maturity of a fetus.

9. The test kit of claim 8 wherein the control samples comprise a solid agar sample in a transparent vial.

10. The test kit of claim 8 wherein the control samples comprise an aqueous suspension of barium sulfate prepared by the reaction of a barium salt and sulfuric acid in a transparent vial and which includes shaking the control sample suspension prior to comparing the amniotic fluid test sample with the control samples.

11. The test kit of claim 8 wherein the positive control sample comprises about 3.0% by weight of purified agar in water and the negative control sample comprises about 0.75% by weight of purified agar in water.

12. The test kit of claim 8 includes the positive and negative control samples contained in transparent vials and the test sample contained in a transparent vial, where the test sample vial is adjacent to or between the control sample vials for comparison and all the vials are compared against a selected background means.

* * * * *